USOO5652223A

United States Patent [19]
Kohn et al.

[11] Patent Number: 5,652,223
[45] Date of Patent: Jul. 29, 1997

[54] DNA ENCODING CAI RESISTANCE PROTEINS AND USES THEREOF

[75] Inventors: Elise C. Kohn, Olney; Lance A. Liotta, Potomac; Young Sook Kim, Bethesda, all of Md.

[73] Assignee: The United States of America as represented by the Secretary of the Department of Health and Human Services, Washington, D.C.

[21] Appl. No.: 212,190

[22] Filed: Mar. 14, 1994

[51] Int. Cl.$^6$ .......................... A01N 43/04; A61K 31/70; C12N 5/10
[52] U.S. Cl. .......................... 514/44; 536/23.1; 536/23.2; 536/23.5; 435/91.1; 435/91.5; 435/172.3; 435/320.1; 935/9; 935/14
[58] Field of Search .......................... 536/23.1, 23.2, 536/23.5; 514/44; 435/91.5, 91.1, 240.2, 320.1, 172.3; 935/9, 14

[56] References Cited

U.S. PATENT DOCUMENTS 5,359,078 10/1994 Kohn et al. .......................... 548/255

OTHER PUBLICATIONS

Asubel et al. (eds.), 1988, in: Current Protocols In Molecular Biology, John Wiley & Sons, New York, pp. 6.3.2 to 6.3.6, 6.4.1 to 6.4.3, and A.2.3.
Federal Res. in Progress (Dialog File 265)—"Signal Transduction Therapy Basic Science. Princ. Invest.", Kohn, E.C., Research Summary, Identification 1Z01CB09163-06.
Baker et al. 1987. in: Fourth Edition. *The Study of Biology*. Addison-Wesley Publ. Co., Reading MA., p. 520.
Forgue-Lafitte et al. 1992 Cancer Res. 52, 6827-6831.
Hampson et al. 1992 Nuc. Acids Res. 20, 2899.
Kohn, et al., *Cancer Res.*, 54: 935-942 (1994).
Kohn & Liotta, *J. Nat. Cancer Inst.*, 82: 54-60 (1990).
Kim, et al., *Proc. Am. Assoc. for Cancer Res.*, 35: 591 (1994).
Felder, et al., *J. Pharm. Exp. Therap.*, 257: 967-971 (1991).
Gusovsky, et al., *J. Bio. Chem.*, 268: 7768-7772 (1993).
Merritt, et al., *Biochem. J.*, 271: 515-522 (1990).
Cicchetti, et al., *Science*, 257: 803-806 (1992).
Ren, et al., *Science*, 259: 1157-1161 (1993).
Kapeller, et al., *J. Biol. Chem.*, 269:3 1927-1933 (1994).
Koch, et al., *Science*, 252: 668-674 (1991).

*Primary Examiner*—Christopher S. F. Low
*Attorney, Agent, or Firm*—Townsend & Townsend & Crew LLP

[57] ABSTRACT

This invention provides for nucleotide sequences that encode CAIR proteins correlated with cellular resistance to carboxyamido-triazole (CAI) and functionally equivalent compounds. The invention further provides for methods of detecting CAI resistance in biological samples and for cell lines that grow and proliferate in the presence of CAI and functionally equivalent compounds.

5 Claims, 1 Drawing Sheet

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 1269 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:

-continued (A) NAME/KEY: misc_feature
(B) LOCATION: 1..1269
(D) OTHER INFORMATION: /standard_name= "CAIR-1 cDNA"

(xi) SEQUENCE DESCRIPTION: SEQ ID NO:1:

```
GGCACGAGTT CAAGTGATCC GCAAAGAGGT GGATTCTAAA CCTGTTTCCC AGAAGCCCCC      60
ACCTCCCTCT GAGAAGGTAG AGGTGAAAGT TCCCCCTGCT CCAGTTCCTT GTCCTCCTCC     120
CAGCCCTGGC CCTTCTGCTG TCCCTCTTC  CCCCAAGAGT GTGGCTACAG AAGAGAGGGC     180
AGCCCCCAGC ACTGCCCCTG CAGAAGCTAC ACCTCCAAAA CCAGGAGAAG CCGAGGCTCC     240
CCCAAAACAT CCAGGAGTGC TGAAAGTGGA AGCCATCCTG GAGAAGGTGC AGGGGCTGGA     300
GCAGGCTGTA GACAACTTTG AAGGCAAGAA GACTGACAAA AAGTACCTGA TGATCGAAGA     360
GTATTTGACC AAAGAGCTGC TGGCCCTGGA TTCAGTGGAC CCCGAGGGAC GAGCCGATGT     420
GCGTCAGGCC AGGAGAGACG TGTCAGGAA  GGTTCAGACC ATCTTGGAAA AACTTGAACA     480
GAAAGCCATT GATGTCCCAG GTCAAGTCCA GGTCTATGAA CTCCAGCCCA GCAACCTTGA     540
AGCAGATCAG CCACTGCAGG CAATCATGGA GATGGGTGCC GTGGCAGCAG ACAAGGGCAA     600
GAAAAATGCT GGAAATGCAG AAGATCCCCA CACAGAAACC CAGCAGCCAG AAGCCACAGC     660
AGCAGCGACT TCAAACCCCA GCAGCATGAC AGACACCCCT GGTAACCCAG CAGCACCGTA     720
GCCTCTGCCC TGTAAAAATC AGACTCGGAA CCGATGTGTG CTTTAGGGAA TTTTAAGTTG     780
CATGCATTTC AGAGACTTTA AGTCAGTTGG TTTTTATTAG CTGCTTGGTA TGCAGTAACT     840
TGGGTGGAGG CAAAACACTA ATAAAAGGGC TAAAAAGGAA AATGATGCTT TTCTTCTATA     900
TTCTTACTCT GTACAAATAA AGAAGTTGCT TGTTGTTTCA GAAGTTTAAC CCCGTTGCTT     960
GTTCTGCAGC CCTGTCTACT TGGGCACCCC CACCACCTGT TAGCTGTGGT TGTGCACTGT    1020
CTTTTGTAGC TCTGGACTGG AGGGGTAGAT GGGGAGTCAA TTACCCATCA CATAAATATG    1080
AAACATTTAT CAGAAATGTT GCCATTTAA  TGAGATGATT TTCTTCATCT CATAATTAAA    1140
ATACCTGACT TTAGAGAGAG TAAAATGTGC CAGGAGCCAT AGGAATATCT GTATGTTGGA    1200
TGACTTTAAT GCTACATTTT AAAAAAGAA  AATAAAGTAA TAATATAACT CAAAAAAAA     1260
AAAAAAAA                                                             1269
```

(2) INFORMATION FOR SEQ ID NO:2:

(i) SEQUENCE CHARACTERISTICS:
(A) LENGTH: 241 amino acids
(B) TYPE: amino acid
(C) STRANDEDNESS: unknown
(D) TOPOLOGY: unknown (ii) MOLECULE TYPE: protein (ix) FEATURE:
(A) NAME/KEY: Protein
(B) LOCATION: 1..241
(D) OTHER INFORMATION: /note= "CAIR-1 PROTEIN"

(xi) SEQUENCE DESCRIPTION: SEQ ID NO:2:

```
Asn Ser Ala Arg Val Gln Val Ile Arg Lys Glu Val Asp Ser Lys Pro
 1               5                  10                  15
Val Ser Gln Lys Pro Pro Pro Ser Glu Lys Val Glu Val Lys Val
                20              25                  30
Pro Pro Ala Pro Val Pro Cys Pro Pro Ser Pro Gly Pro Ser Ala
                35              40                  45
Val Pro Ser Ser Pro Lys Ser Val Ala Thr Glu Glu Arg Ala Ala Pro
        50                  55                  60
```

| | | | | | | | | | | | | | | | |
|---|---|---|---|---|---|---|---|---|---|---|---|---|---|---|---|
| Ser 65 | Thr | Ala | Pro | Ala | Glu 70 | Ala | Thr | Pro | Pro 75 | Lys | Pro | Gly | Glu | Ala | Glu 80 |
| Ala | Pro | Pro | Lys | His 85 | Pro | Gly | Val | Leu | Lys 90 | Val | Glu | Ala | Ile | Leu 95 | Glu |
| Lys | Val | Gln | Gly 100 | Leu | Glu | Gln | Ala | Val 105 | Asp | Asn | Phe | Glu | Gly 110 | Lys | Lys |
| Thr | Asp | Lys 115 | Lys | Tyr | Leu | Met | Ile 120 | Glu | Glu | Tyr | Leu | Thr 125 | Lys | Glu | Leu |
| Leu | Ala 130 | Leu | Asp | Ser | Val | Asp 135 | Pro | Glu | Gly | Arg | Ala 140 | Asp | Val | Arg | Gln |
| Ala 145 | Arg | Arg | Asp | Gly | Val 150 | Arg | Lys | Val | Gln | Thr 155 | Ile | Leu | Glu | Lys | Leu 160 |
| Glu | Gln | Lys | Ala | Ile 165 | Asp | Val | Pro | Gly | Gln 170 | Val | Gln | Val | Tyr | Glu 175 | Leu |
| Gln | Pro | Ser | Asn 180 | Leu | Glu | Ala | Asp | Gln 185 | Pro | Leu | Gln | Ala | Ile 190 | Met | Glu |
| Met | Gly | Ala 195 | Val | Ala | Ala | Asp | Lys 200 | Gly | Lys | Lys | Asn | Ala 205 | Gly | Asn | Ala |
| Glu | Asp 210 | Pro | His | Thr | Glu | Thr 215 | Gln | Gln | Pro | Glu | Ala 220 | Thr | Ala | Ala | Ala |
| Thr 225 | Ser | Asn | Pro | Ser | Ser 230 | Met | Thr | Asp | Thr | Pro 235 | Gly | Asn | Pro | Ala | Ala 240 |
| Pro | | | | | | | | | | | | | | | |

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "X is any amino acid."

( i x ) FEATURE:
        ( A ) NAME/KEY: Region
        ( B ) LOCATION: 2
        ( D ) OTHER INFORMATION: /note= "P is obligate proline."

( i x ) FEATURE:
        ( A ) NAME/KEY: Modified-site
        ( B ) LOCATION: 3
        ( D ) OTHER INFORMATION: /note= "X is any amino acid."

( i x ) FEATURE:
        ( A ) NAME/KEY: Modified-site
        ( B ) LOCATION: 4
        ( D ) OTHER INFORMATION: /note= "X is any amino acid."

( i x ) FEATURE:
        ( A ) NAME/KEY: Region
        ( B ) LOCATION: 5
        ( D ) OTHER INFORMATION: /note= "P is an obligate proline."

( i x ) FEATURE:
        ( A ) NAME/KEY: Region
        ( B ) LOCATION: 6
        ( D ) OTHER INFORMATION: /note= "P is an obligate proline."

( i x ) FEATURE:
        ( A ) NAME/KEY: Modified-site
        ( B ) LOCATION: 7
        ( D ) OTHER INFORMATION: /note= "P is an obligate proline."

(i x) FEATURE:
    (A) NAME/KEY: Modified-site
    (B) LOCATION: 8
    (D) OTHER INFORMATION: /note= "X is a hydrophobic amino acid."

(i x) FEATURE:
    (A) NAME/KEY: Modified-site
    (B) LOCATION: 9
    (D) OTHER INFORMATION: /note= "X is any amino acid."

(i x) FEATURE:
    (A) NAME/KEY: Region
    (B) LOCATION: 10
    (D) OTHER INFORMATION: /note= "P is an obligate proline."

(x i) SEQUENCE DESCRIPTION: SEQ ID NO:3:

```
Xaa  Pro  Xaa  Xaa  Pro  Pro  Pro  Xaa  Xaa  Pro
 1               5                         10
```

(2) INFORMATION FOR SEQ ID NO:4:

(i) SEQUENCE CHARACTERISTICS:
        (A) LENGTH: 10 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:4:

```
Lys  Pro  Val  Ser  Asp  Lys  Pro  Pro  Pro  Pro
 1               5                         10
```

(2) INFORMATION FOR SEQ ID NO:5:

(i) SEQUENCE CHARACTERISTICS:
        (A) LENGTH: 10 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:5:

```
Val  Pro  Pro  Ala  Pro  Val  Pro  Cys  Pro  Pro
 1               5                         10
```

(2) INFORMATION FOR SEQ ID NO:6:

(i) SEQUENCE CHARACTERISTICS:
        (A) LENGTH: 10 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:6:

```
Ala  Pro  Val  Pro  Cys  Pro  Pro  Pro  Ser  Pro
 1               5                         10
```

(2) INFORMATION FOR SEQ ID NO:7:

(i) SEQUENCE CHARACTERISTICS:
        (A) LENGTH: 10 amino acids
        (B) TYPE: amino acid
        (C) STRANDEDNESS: single
        (D) TOPOLOGY: linear (i i) MOLECULE TYPE: peptide ( x i ) SEQUENCE DESCRIPTION: SEQ ID NO:7:

Ala Pro Ala Glu Ala Thr Pro Pro Lys Pro
1               5                   10

( 2 ) INFORMATION FOR SEQ ID NO:8:

( i ) SEQUENCE CHARACTERISTICS:
   ( A ) LENGTH: 10 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:8:

Ala Pro Thr Met Pro Pro Pro Leu Pro Pro
1               5                   10

( 2 ) INFORMATION FOR SEQ ID NO:9:

( i ) SEQUENCE CHARACTERISTICS:
   ( A ) LENGTH: 10 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:9:

Ala Pro Pro Thr Pro Lys Pro Arg Pro Pro
1               5                   10

( 2 ) INFORMATION FOR SEQ ID NO:10:

( i ) SEQUENCE CHARACTERISTICS:
   ( A ) LENGTH: 10 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:10:

Gln Pro Ala Pro Ala Leu Pro Pro Lys Pro
1               5                   10

DNA ENCODING CAI RESISTANCE PROTEINS AND USES THEREOF

FIELD OF THE INVENTION

The present invention relates to the isolation of a CAI resistance (CAIR) gene that encodes a protein conferring cellular resistance to carboxyamido-triazole (CAI) and functionally equivalent compounds. This invention further relates to the CAIR protein encoded by the CAI resistance gene, antibodies specific to the protein, and nucleic acid probes that specifically hybridize to the gene. Additionally the invention provides assays for determining CAI resistance in cells, and assays to screen for compositions that obviate CAI resistance. The invention also provides for cell lines that express the CAIR gene and are capable of growing and proliferating in cultures chronically exposed to CAI and functionally equivalent compounds.

BACKGROUND OF THE INVENTION

Calcium homeostasis is important in the regulation of cellular behavior as it is paramount in regulation of signaling events as well as other cellular and molecular functions. (Cole and Kohn, *Cancer and Metastasis Rev.* (1993). Carboxyamido-triazole (CAI) is an inhibitor of stimulated calcium influx through voltage gated and nonvoltage-gated calcium influx. It has been shown to inhibit important downstream signaling events including the release or arachidonic acid, production of inositol triphosphate in response to phosphorylation and activation of phospholipase A2, and tyrosine phosphorylation in response to receptor activation (Felder, et al. *J. Pharm. Exp. Therap.*, 257:967–971 (1991); Gusovsky, et al. *J. Bio. Chem.*, 268:7768–7772 (1993)). These signalling pathways regulate proliferation and other cellular events including adhesion, migration, and production of proteases. (Kohn, et al. *Cancer Res.* (1994) in press, Kohn, et al. *Proc. Natl. Acad. Sci. U.S.A.*, communicated; Kohn and Liotta, *J. Nat. Cancer Inst.*, 82:54–60 (1990)).

Carboxyamido-triazole (CAI) has been observed to inhibit malignant proliferation, invasion, and metastasis of cancer cells, suggesting the role of CAI, and related compounds, as potential cancer therapeutics (see U.S. Pat. No. 5,359,078). Of concern in the development and utilization of cancer therapeutics is the development of resistance by minor cells to the particular pharmacological regimen to which they are exposed.

Where such a resistance appears it is desirable to ascertain the resistance in order to devise therapeutics that obviate or prohibit the appearance of such resistance. When the resistance is associated with altered gene expression, isolation of the gene encoding proteins associated with the appearance of the resistance not only aids in the elucidation of the mechanism of drug resistance, but also provides useful markers for detecting the acquisition of the resistance as well as useful targets for intervention. The present invention provides an isolated CAI resistance (CAIR) gene whose expression is correlated with CAI resistance. This invention also provides for the protein encoded by this gene. The isolation of this gene and protein provide the aforementioned and other advantages.

SUMMARY OF THE INVENTION

The present invention provides for an isolated human nucleic acid encoding a human carboxyamido-triazole resistance (CAIR) protein where the nucleic acid is capable of hybridizing specifically to a second nucleic acid consisting of the nucleic acid sequence of Seq. Id. No. 1 in the presence of a human genomic library under stringent conditions. Specifically this nucleic acid comprises the nucleotide sequence of Seq. Id. No. 1. More particularly, the isolated nucleic acid, when found in a cell line, expresses the protein it encodes at higher levels when the cell line is cultured in the presence of at least 10 µM concentration of CAI than when the cell line is cultured under the same culture conditions without CAI.

The invention also provides for an isolated human nucleic acid sequence encoding a CAIR protein, wherein the nucleic acid sequence has at least 85%, more particularly at least 95% sequence identity with the nucleic acid of Seq. Id. No. 1. The isolated human nucleic acid sequence, when found in a cell line, expresses the protein it encodes at higher levels when the cell line is cultured in the presence of at least 10 µM concentration of CAI than when the cell line, is cultured under the same culture conditions without CAI.

This invention additionally provides for an isolated human nucleic acid encoding a CAIR protein having at least 80%, more particularly at least 95% amino acid identity with the amino acid sequence of Seq. Id. No. 2. This isolated human nucleic acid, when found in a cell line, expresses the protein it encodes at higher levels when the cell line is cultured in the presence of at least 10 µM concentration of CAI than when the line is cultured under the same culture conditions without CAI.

In another embodiment, this invention provides for an isolated CAIR protein that has at least 80% sequence identity, more particularly at least 95% sequence identity with the amino acid sequence of Seq. Id. No. 2. This isolated CAIR protein, when expressed in a cell line, is expressed at higher levels when the cell line is cultured in the presence of at least 10 µM concentration of CAI than when the cell line is cultured under the same culture conditions without CAI.

This invention provides for an isolated CAIR protein, wherein the protein specifically binds to an antibody generated against an immunogen consisting of the amino acid sequence depicted by Seq. Id No. 2. More specifically the carboxyl terminus of the protein consists of a polypeptide of Seq. Id No. 2. In addition, the protein may be recombinantly produced. This protein is expressed at higher levels in a cell line cultured in the presence of at least 10 µM concentration of CAI than in the cell line cultured under the same culture conditions without CAI.

In still another embodiment, this invention provides for an isolated nucleic acid encoding a CAIR resistance protein, wherein the protein specifically binds to an antibody generated against an immunogen consisting of the amino acid sequence depicted by Seq. Id No. 2. More specifically this nucleic acid comprises the nucleotide sequence of Seq. Id No. 1.

In yet another embodiment, this invention provides for cells capable of growing and proliferating when cultured in the presence of CAI ranging in concentration from 1 µM to 45 µM, more particularly in CAI ranging in concentration from 20 µM to 45 µM, and still more particularly in CAI ranging in concentration from 40 µM to 45 µM. Even more particularly these cells are A2058-20R cells or OVCAR3-R cells.

This invention additionally provides for a method of determining resistance of CAI of a biological sample where the method comprises the steps of a) contacting a binding agent capable of specifically binding a CAI resistance protein to the biological sample; b) incubating the binding agent with the biological sample to form a binding agent:CAIR protein complex; and c) detecting the complex. More particularly, the binding agent is an antibody that is specifically immunoreactive with the CAI resistance protein. Even more particularly, the step of detecting comprises a) contacting the complex with a labeled antibody that specifically binds the binding agent; and b) detecting the labeled antibody.

In another embodiment, this invention provides for a method of determining resistance of CAI of a biological sample where the method comprises the steps of a) contacting a binding agent capable of specifically binding nucleotide sequence that encodes a CAI resistance protein with the biological sample; b) incubating the binding agent with the biological sample to form a binding agent:nucleic acid complex; and c) detecting the complex. More particularly, the binding agent is a nucleic acid that hybridizes specifically to a second nucleic acid sequence that encodes a CAI resistance protein under stringent conditions. Even more particularly, the nucleic acid hybridizes specifically to a DNA sequence of sequence Id number 1. Still more particularly, the step of detecting comprises detecting a labeled nucleic acid.

This invention provides for a kit for determining the resistance to CAI where the kit comprises a container containing a binding agent capable of specifically binding a CAIR protein. More particularly, the binding agent of the kit is an antibody that specifically binds to a CAIR protein. Even more particularly, the kit further comprises a container containing a means for detecting the antibody.

In another embodiment, the invention provides for a kit for determining resistance to CAI of a biological sample where the kit comprises a container containing a binding agent capable of specifically binding a nucleic acid sequence encoding a CAI resistance protein. More particularly, the binding agent is a second nucleic acid that hybridizes specifically to the nucleic acid sequence under stringent conditions.

The invention also provides for a kit for assaying compounds for a CAI resistance obviating activity, where the kit comprises a container containing a CAI resistant cell. More particularly the cell is A2058-20R or OVCAR3-R.

The invention provides for an antibody that specifically binds to a CAIR protein. More particularly, these antibody is generated against an immunogen consisting of the amino acid sequence depicted by Sequence. Id Number 2.

In another embodiment, this invention provides for a pharmacological composition that reduces CAI resistance said composition comprising a binding agent that binds to a nucleotide encoding a CAIR protein. More particularly the binding agent is an antisense molecule that hybridizes specifically to a nucleotide encoding a CAIR protein. Even more particularly the nucleotide encoding a CAIR protein is Seq. Id. No. 1

DESCRIPTION OF THE PREFERRED EMBODIMENT

Definitions

Figure 1:
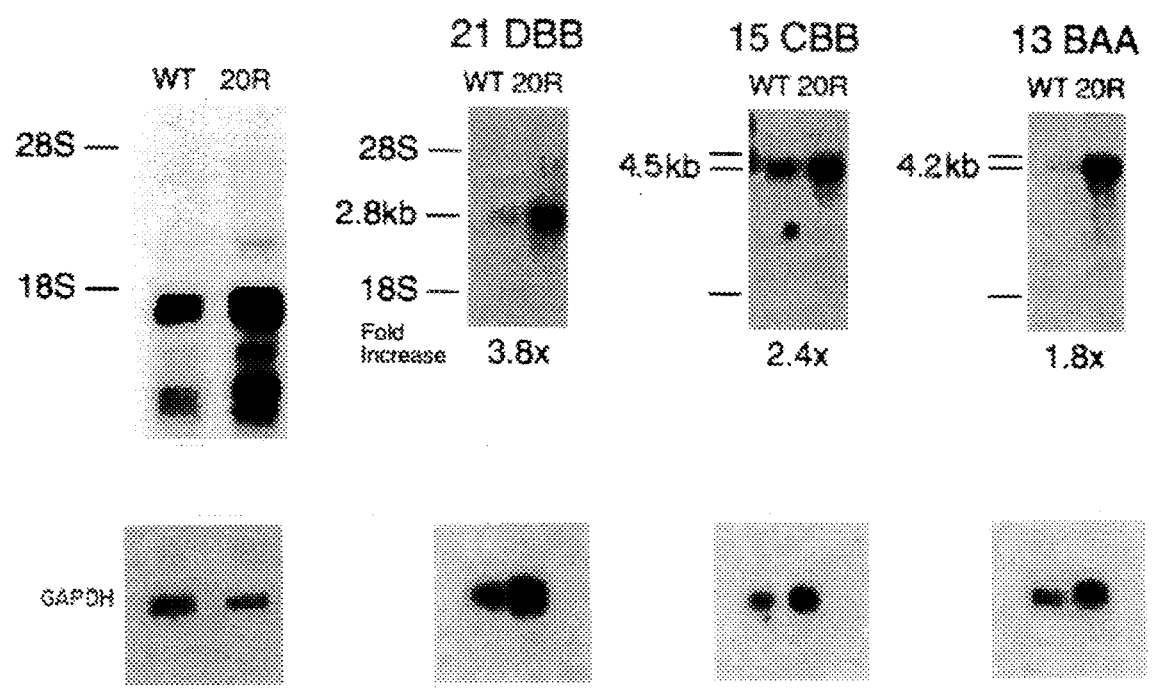
FIG. 1 shows Northern analyses indicating up-regulation of the CAIR gene. The upper left gel shows a Northern blot of total RNA from parental A2058 cells hybridized to a probe obtained from a subtractive hybridization of A2058-20R CAI resistant cells against parental A2058 cells. A cDNA library was created from A2058-20R cells and screened with the subtracted probe. The selected clones when hybridized against Northern blots identified altered gene expression in response to chronic exposure to CAI. The gels labeled 21 DBB (CAIR-1), 15 CBB (CAIR-3) and 13 BAA (CAIR-2) represent clones showing increased expression in response to CAI exposure. The transcribed message of CAIR-1 is about 2.8 kb, while the messages for CAIR3 and CAIR-2 are about 4.5 kb and 4.2 kb respectively. In all cases, the blots were stripped and then rehybrizided with radiolabeled GAPDH as a housekeeping gene to correct for differential loading (lower gels).

Abbreviations for the twenty naturally occurring amino acids follow conventional usage. In the polypeptide notation used herein, the left-hand direction is the amino terminal direction and the right-hand direction is the carboxy-terminal direction, in accordance with standard usage and convention.

The term "CAI resistance" as used herein refers to the ability of a cell to grow and proliferate in the presence of carboxyamido-triazole (CAI) and functionally equivalent compositions at a concentration of 10 μM or greater. Functionally equivalent compositions are those compositions that act in a manner identical to or analogous to CAI in inhibiting calcium influx. Although the specific activity levels of the functionally equivalent compositions may differ, they produce the same biological effects. These include inhibition of calcium influx and consequent reduction in cell proliferation rate. Examples of functionally equivalent compositions include the antimycotic imidizoles such as ketoconazole, miconazole, fluconazole, econazole and itraconazole, the compound described by Merritt, et al., *Biochem. J.*, 271:515–522 (1990) and its analogs. These analogs, described in copending patent application U.S. Ser. No. 07/985,402, include compounds of the formula:

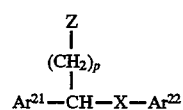

in which $Ar^{21}$ and $Ar^{22}$ may be the same or different and are either phenyl, napthyl, or their substituted analogs; X is O, S, SO, CO, CHCN, straight chain alkyl, alkoxy and alkoxyalkyl; Z is a nitrogen-containing heterocycle such as imidizolyl, 1,2,3-triazolyl, 1,2,3-triazolyl, 1,2,4-triazolyl, pyrazinyl, purinyl, pyrimidinyl, 1,2,3-triazolo-{4,5-d-}-pyrimidinyl, or a substituted analog thereof; and p is an integer of from 0 to 4.

A "CAI resistance protein" or "CAIR protein" refers to a protein whose expression in a cell is correlated with the ability of a cell to display CAI resistance. That is, to grow and proliferate in the presence of CAI and functionally equivalent compositions. The CAIR-1 resistance protein of this invention is characterized by at least one proline rich domain, a novel domain homologous to the Src homology 3 (SH3) binding domain consensus sequence. The SH3 binding protein domain consensus sequence is XPXXPPPψXP where positions 2, 7 and 10 are obligate P (proline), the X is any amino acid, and the ψ is a hydrophobic amino acid. The CAIR proteins of this invention are up-regulated when the cell is exposed to CAI and this up-regulation is characteristic of and correlated with CAI resistance.

The term "nucleic acid" refers to a deoxyribonucleotide or ribonucleotide polymer in either single- or double-stranded form, and unless otherwise limited, would encompass known analogs of natural nucleotides that can function in a similar manner as naturally occurring nucleotides.

The phrase "nucleic acid encoding" or "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both full length nucleic acid sequences as well as shorter sequences derived from the full length sequences. It is understood that a particular nucleic acid sequence includes the degenerate codons of the native sequence or sequences which may be introduced to provide codon preference in a specific host cell. The nucleic acid includes both the sense and antisense strands as either individual single strands or in the duplex. The terms "hybridize" or "hybridizing" refer to the binding of two single strangled nucleic acids via complementary base pairing.

The phrase "hybridizing specifically to", refers to the binding, duplexing, or hybridizing of a molecule only to a particular nucleotide sequence under stringent conditions when that sequence is present in a preparation of total cellular DNA or RNA.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a complementary probe. Typically, stringent conditions will be those in which the salt concentration is at least about 0.1 to 1.0N Na ion concentration at pH 7.0 to 7.5 and the temperature is at least about 60° C. for long sequences (e.g. greater than about 50 nucleotides) and at least about 42° C. for shorter sequences (e.g. 10 to 50 nucleotides).

The terms "isolated" or "substantially pure" when referring to nucleic acid sequences encoding CAIR proteins or fragments thereof refers to isolated nucleic acids which do not encode proteins or peptides other than CAIR proteins or peptides.

The terms "isolated" or "substantially purified" or "isolated" when referring to a CAIR proteins, means a chemical composition which is essentially free of other cellular components. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. Generally, a substantially purified or isolated protein will comprise more than 80% of all macromolecular species present in the preparation. Preferably, the protein is purified to represent greater than 90% of all macromolecular species present. More preferably the protein is purified to greater than 95%, and most preferably the protein is purified to essential homogeneity, wherein other macromolecular species are not detected by conventional techniques.

The phrase "specifically binds to an antibody" or "specifically immunoreactive with", when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised to the CAI protein fragment with the amino acid sequence depicted in Seq. Id No. 2 can be selected to obtain antibodies specifically immunoreactive with CAIR proteins and not with other proteins. These antibodies recognize proteins homologous to the CAIR protein. Homologous proteins encompass the family of CAIR proteins, but do not include other signal transduction proteins that are not up-regulated in response to exposure to CAI. A variety of immunoassay formats may be used to select antibodies specifically immunoreactive with a particular protein. For example, solid-phase ELISA immunoassays are routinely used to select antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

The term "binding agent:CAIR protein complex", as used herein, refers to a complex of a binding agent and a CAIR protein that is formed by specific binding of the binding agent to the CAIR protein. Specific binding of the binding agent means that the binding agent has a specific binding site that recognizes a site on the CAIR protein. For example, antibodies raised to a CAIR protein and recognizing an epitope on the CAIR protein are capable of forming a binding agent:CAIR protein complex by specific binding. Typically, the formation of a binding agent:CAIR protein allows the measurement of CAIR protein in a mixture of other proteins and biologics. The term "antibody:CAIR protein complex" refers to a binding agent:CAIR protein complex in which the binding agent is an antibody.

The term "binding agent:nucleic acid complex", as used herein, refers to a complex of a binding agent and a nucleic acid that is formed by specific binding of the binding agent to the nucleic acid. Specific binding of the binding agent means that the binding agent has a specific binding site that recognizes a site on the CAIR protein. For example, nucleic acid probes complementary to a region of the nucleic acid sequence encoding a CAIR protein are capable for forming a probe:CAI nucleic acid complex.

The term "biological sample" as used herein refers to any sample obtained from a living organism or from an organism that has died. Examples of biological samples include body fluids, tissue specimens, and tissue culture lines taken from patients.

The term "recombinant DNA" or "recombinantly produced DNA" refers to DNA which has been isolated from its native or endogenous source and modified either chemically or enzymatically to delete naturally-occurring flanking nucleotides or provide flanking nucleotides that do not naturally occur. Flanking nucleotides are those nucleotides which are either upstream or downstream from the described sequence or sub-sequence of nucleotides.

The term "recombinant protein" or "recombinantly produced protein" refers to a peptide or protein produced using non-native cells that do not have an endogenous copy of DNA able to express the protein. The cells produce the protein because they have been genetically altered by the introduction of the appropriate nucleic acid sequence. The recombinant protein will not be found in association with proteins and other subcellular components normally associated with the cells producing the protein.

The following terms are used to describe the sequence relationships between two or more nucleic acids or polynucleotides: "reference sequence", "comparison window", "sequence identity", and "percentage of sequence identity".

A "reference sequence" is a defined sequence used as a basis for a sequence comparison; a reference sequence may be a subset of a larger sequence, for example, as a segment of a full-length cDNA or gene sequence given in a sequence listing, such as the nucleic acid sequence of Seq. Id No. 1, or may comprise a complete cDNA or gene sequence.

"Percentage of sequence identity" is determined by comparing two optimally aligned sequences or subsequences over a comparison window or span, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical subunit (e.g. nucleic acid base or amino acid residue) occurs in both sequences to yield the number of matched positions, dividing the number of matched positions by the total number of positions in the window of comparison and multiplying the result by 100 to yield the percentage of sequence identity. Percentage sequence identity when calculated using the programs GAP or BESTFIT (see below) is calculated using default gap weights.

When percentage of sequence identity is used in reference to proteins or peptides it is recognized that residue positions which are not identical may differ by conservative amino acid substitutions, where amino acids residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to the algorithm of Meyers and Miller, *Computer Applic. Biol. Sci.*, 4:11–17 (1988) as implemented in the program PC/GENE (Intelligenetics, Moutain View, Calif., U.S.A.). The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Argenine (R), Lysine (K);
5) Isoleucine (I), Leucine (L), Methionine (M), Valine (V); and
6) Phynylalanine (F), Tyrosine (Y), Tryptophan (W).

A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are optimally aligned.

Methods of alignment of sequences for comparison are well known in the art. Optimal alignment of sequences for comparison may be conducted by the local homology algorithm of Smith and Waterman, *Adv. Appl. Math.* 2:482 (1981) which is incorporated herein by reference, by the homology alignment algorithm of Needleman and Wunsch *J. Mol. Biol.* 48:443 (1970) which is incorporated herein by reference, by the search for similarity method of Pearson and Lipman, *Proc. Natl. Acad. Sci. U.S.A.* 85:2444 (1988) which is incorporated herein by reference, by computerized implementations of these algorithms (including, but not limited to CLUSTAL in the PC/Gene program by Intelligenetics, Moutain View, Calif., GAP, BESTFIT, FASTA, and TFASTA in the Wisconsin Genetics Software Package, Genetics Computer Group (GCG), 575 Science Dr., Madison, Wis., U.S.A.), or by inspection. In particular, methods for aligning sequences using the CLUSTAL program are well described by Higgins and Sharp in *Gene*, 73:237–244 (1988) and in *CABIOS* 5:151–153 (1989) both of which are incorporated herein by reference.

DETAILED DESCRIPTION

This invention provides for isolated proteins correlated with cellular resistance to carboxyamido-triazole (CAI) and functionally equivalent compositions, and for isolated nucleic acids that encode these proteins. These isolated nucleic acid and protein compositions can be used in a number of applications. For instance, both the protein and the nucleic acid can be used as markers indicating the acquisition of resistance to CAI by tumor cells undergoing CAI chemotherapy. The nucleic acid sequence may also be used as a selectable marker by linking it to another nucleic acid sequence in a vector and transforming a cell line. The transformed cells may be selected by exposing the cells to CAI and selecting those cells that survive.

In addition, at least one CAIR protein, CAIR-1, contains Src homology 3 (SH3) binding domains which interact with SH3 domains on a variety of proteins and may be used to modulate or inactivate various intercellular signaling pathways or cytoskeletal elements. Thus, the protein or fragments bearing SH3 binding domains may be used as therapeutics for disease states characterized by calcium signaling problems. Furthermore, the protein or fragments bearing SH3 binding domains may be used to assay for and identify other proteins carrying SH3 domains and thereby identify new elements in the signalling pathway.

The present invention also provides for antibodies specific to the CAIR proteins. These antibodies may be used to inactivate the protein and thereby obviate CAI resistance. In addition, antibodies that bind the SH3 binding domains may be used to compete with SH3 bearing proteins and thus used to modulate or inhibit various signaling pathways or the action of various cytoskeletal elements.

This invention additionally provides for eel/lines that display CAI resistance. These cell lines may be used as an assay to screen for compounds that can reduce or eliminate CAI resistance. They can also be used as model systems for evaluating the effectiveness of mixed drug regimens that include CAI or analogous calcium regulation inhibitors.

A. Inducing Expression of CAIR Genes

CAIR genes are up-regulated in cells that grow and proliferate when they are challenged with CAI and functionally equivalent compositions. These compounds include the antimycotic imidizoles such as ketoconazole, miconazole, fluconazole, econazole and itraconazole, the compound described by Merritt, et al., *Biochem. J.*, 271: 515–522 (1990) and its analogs as described above.

CAIR genes may be identified by culturing cells in the presence of increasing concentrations of CAI and its functional equivalents. Cells that grow and proliferate are selected, their RNA isolated and a subtraction hybridization is performed against the unchallenged parental cell line. Subtractive hybridization yields a probe which may be labeled and is then used to probe cDNA libraries for clones showing elevated expression of the gene in the presence of CAI or its functional equivalents.

B. CAIR Proteins

The CAI resistance (CAIR) proteins are correlated with cellular CAI resistance. These expression of these proteins is typically up-regulated in cells that survive a challenge with CAI or functionally equivalent compounds.

The carboxyl terminus of one such protein (CAIR-1) is shown in Seq. Id. No.: 2. This protein contains a number of Src homology 3 domain (SH3) binding protein domains. SH3 domains are conserved among a very large group of proteins including cytoskeletal elements and intracellular signaling proteins (Ren, et al., Science 259:1157–1161 (1993)). These domains appear to be involved in the mediation of protein-protein associations and regulate cytoplasmic signaling. Id.

Thus the CAIR-1 protein of this invention or fragments thereof comprising the SH3 binding proteins domains may be used in inhibit or modulate various intracellular signaling pathways. This provides a mode of treatment for various diseases characterized by abnormal intracellular signaling such as cancer, hyperproliferative states, correction of collagen vascularities (e.g. lupis and rheumatoid arthritis), nephropathies, neruopathies (e.g. ALF, Alzheimers disease), and myopathies (e.g. cardiomyopathies, skeletalmyopathies).

Means of identifying SH3 binding domains in CAIR proteins are well known to those of skill in the art. Where the protein sequence is known, regions of the protein whose sequences fulfill the consensus definition for SH3 binding domains (XPXXPPPψXP where positions 2, 7, and 10 are obligate P (proline), the X is any amino acid, and the ψ is a hydrophobic amino acid) may easily be identified either by inspection of through the use of sequence analysis programs such as FASTA or BESTFIT.

SH3 binding sites may also be identified by assaying for actual binding between the CAIR protein and proteins bearing known SH3 sites such as Abl, Fyn, Lck and the p85 α subunit of phosphatidylinositol 3'kinase. Protein binding assays are well known to those of skill in the art. In a preferred embodiment, the assay may be conducted by creating a GST-CAIR-1 fusion protein, immobilizing the protein on glutathione-Sepharose beads, exposing the immobilized protein to the screening proteins (e.g., Abl, Fyn, Lck and p85) and then assaying for binding of the screening proteins. Binding may easily be assayed using labeled monoclonal antibodies specific to the SH3 proteins. These are commercially available. An example of this assay is provided in Example 5.

The CAIR proteins of the present invention also include proteins that may contain various amino acid substitutions, but retain essentially the same conformation and activity as the unmodified protein. Thus, CAIR-1 protein, the carboxyl terminal sequence of which is listed in Seq. Id No. 2, also embraces proteins reflecting conservative amino acid substitutions in the listed sequence. These related proteins may be determined by their sequence identity with the CAIR-1 protein of Sequence Id No. 2. The CAIR proteins of this invention have at least 80 percent sequence identity, preferably at least 90 percent sequence identity, and more preferably at least 95 percent sequence identity as compared to a reference CAIR protein (e.g. Seq. Id. No. 2).

Alternatively, related CAIR proteins may be determined by their cross-reactivity with antibodies generated against a defined immunogen encoded by the CAIR-1 protein of the present invention. A CAIR protein that specifically binds to or that is specifically immunoreactive to an antibody generated against a defined immunogen, such as an immunogen consisting of the amino acid sequence of Seq. Id No. 2, is determined in an immunoassay. The immunoassay uses a polyclonal antiserum which was raised to the protein of Seq. Id No. 2. This antiserum is selected to have low crossreactivity against other non CAIR proteins and any such cross-reactivity is removed by immunoabsorbtion prior to use in the immunoassay.

In order to produce antisera for use in an immunoassay, the protein of Seq. Id No. 2 is isolated as described herein (e.g. the recombinant protein is produced in a mammalian cell line). Then, a mammal (e.g. an inbred swain of mouse such as balb/c) is immunized with the protein of Seq. Id No. 2 using a standard adjuvant, such as Freund's adjuvant, and a standard immunization protocol (see Harlow and Lane, supra). Alternatively, a synthetic peptide derived from the sequences disclosed herein and conjugated to a carrier protein can be used an immunogen. For instance, the peptide of Seq. Id No. 2 may be used. Polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against non-CAIR proteins, using a competitive binding immunoassay such as the one described in Harlow and Lane, supra, at pages 570–573.

Immunoassays in the competitive binding format can be used for the crossreactivity determinations. For example, the protein of Seq. Id No. 2 can be immobilized to a solid support. Proteins added to the assay compete with the binding of the antisera to the immobilized antigen. The ability of the above proteins to compete with the binding of the antisera to the immobilized protein is compared to the protein of Seq. Id No. 2. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoabsorbtion with the above-listed proteins.

The immunoabsorbed and pooled antisera are then used in a competitive binding immunoassay as described above to compare a second protein to the immunogen protein (the CAIR protein of Seq. Id No. 2). In order to make this comparison, the two proteins are each assayed at a wide range of concentrations and the amount of each protein required to inhibit 50% of the binding of the antisera to the immobilized protein is determined. If the mount of the second protein required is less than 10 times the mount of the protein of Seq. Id No. 2 that is required, then the second protein is said to specifically bind to an antibody generated to an immunogen consisting of the protein of Seq. Id No. 2.

It is understood that CAIR proteins refer to a family of related proteins. For a particular gene product, such as CAIR-1 protein, the term refers not only to the amino acid sequences disclosed herein, but also to other proteins that are allelic, non-allelic or species variants. It also understood that the term "CAIR proteins" includes nonnatural mutations introduced by deliberate mutation using conventional recombinant technology such as single site mutation or by excising short sections of DNA encoding CAIR proteins or by substituting new amino acids or adding new amino acids. Such minor alterations must substantially maintain the immunoidentity of the original molecule and/or its biological activity. Thus, these alterations include proteins that are specifically immunoreactive with a designated naturally occurring CAIR protein, for example, the CAIR-1 protein shown in Seq. Id No. 2. The biological properties of the altered proteins can be determined by expressing the protein in an appropriate cell line and challenging the cell in culture with CAI. Particular protein modifications considered minor would include conservative substitutions, that is substitution of amino acids of similar chemical properties, e.g., glutamic acid for aspartic acid or glutamine for asparagine. By aligning a protein optimally with the protein of Seq. Id No. 2 and by using the conventional immunoassays described herein to determine immunoidentity cell growth assays to determine biological activity, one can readily determine the protein compositions of the invention.

CAIR proteins designated by their tissue of origin refer to the gene-product from this family that is predominantly expressed in that tissue. For instance, the term "skeletal muscle CAIR protein" refers to the CAIR protein that is expressed in skeletal tissue. As another example, the term "heart CAIR protein" refers to the CAIR protein expressed in heart tissue. Since CAIR proteins represent a family of related proteins, the proteins expressed in different tissues can be the product of different genes in the family.

C. Nucleic Acids Encoding CAIR Proteins

This invention relates to isolated nucleic acid sequences encoding CAIR proteins. The nucleic acid compositions of this invention, whether RNA, cDNA, genomic DNA, or a hybrid of the various combinations, may be isolated from natural sources or may be synthesized in vitro. The nucleic acids claimed may be present in transformed or transfected whole cells, in a transformed or transfected cell lysate, or in a partially purified or substantially pure form.

The nucleic acid sequences of the invention are typically identical to or show at least 85 percent sequence identity, preferably at least 90 to 95 percent sequence identity, and more preferably at least 99 percent sequence identity (determined as described above) to the nucleic acid sequence of Seq. Id. No. 1. Nucleic acids encoding mammalian CAIR-1 proteins will typically hybridize to the nucleic acid sequence of Seq. Id No. 1 under stringent conditions. For example, nucleic acids encoding CAIR proteins will hybridize to the nucleic acid of sequence Id No. 1 under the hybridization and wash conditions of 50% formamide at 42° C. Other stringent hybridization conditions may also be selected. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.1 to 1.0N Na ion concentration at pH 7.0 to 7.5 and the temperature is at least about 60° C. As other factors may significantly affect the stringency of hybridization, including, among others, base composition and size of the complementary strands, the presence of organic solvents and the extent of base mismatching, the combination of parameters is more important than the absolute measure of any one.

Techniques for nucleic acid manipulation of genes encoding the CAIR proteins such as subcloning nucleic acid sequences encoding polypeptides into expression vectors, labeling probes, DNA hybridization, and the like are described generally in Sambrook, et al., *Molecular Cloning—A Laboratory Manual* (2nd Ed.), Vol. 1–3, Cold Spring Harbor Laboratory, Cold Spring Harbor, N.Y., 1989, which is incorporated herein by reference. This manual is hereinafter referred to as "Sambrook, et al.".

In general nucleic acids encoding CAIR proteins may be obtained by first producing a cell line in which the expression of CAIR proteins are up-regulated. This is accomplished by culturing the cells in the presence of CAI or a functional equivalent as described in section (A) and in Example 1.

A subtraction probe is then obtained by subtractive hybridization between, CAI resistant cells obtained in the culture and the non-resistant parental cell line. Methods of subtractive hybridization are well known to those of skill in the art. See, for example, Hampson, et al., *Nucleic Acids Res.*, 20:2899 (1992), and Example 2.

The resistant cell line is then used to produce a cDNA library which may then be probed using the labeled subtraction probe. Positive clones are then isolated and those clones are screened for up-regulated expression of CAIR proteins using the labeled subtraction probe. Clones showing up-regulated CAIR protein expression may then be sequenced using standard techniques.

Sequence listing number 1 provides the nucleotide sequence obtained in this manner for 1269 bases of the 3' end of the CAIR-1 gene obtained from A2058-20R cells. This represents about 40% of the full length message which is approximately 2.8 kb as determined from the Northern blot (FIG. 1). This sequence listing may be used to obtain the full length sequence using numerous methods well known to those of skill in the art.

For example, various methods of amplifying target sequences, such as the polymerase chain reaction, can also be used to prepare DNA encoding CAIR resistance protein. Polymerase chain reaction (PCR) technology is used to amplify such nucleic acid sequences directly from mRNA, from cDNA, and from genomic DNA libraries or cDNA libraries. The isolated sequences encoding CAIR proteins may also be used as templates for PCR amplification.

In PCR techniques, oligonucleotide primers complementary to either the 5' or the 3' borders of the DNA region to be amplified are synthesized, or random primers may be used. The polymerase chain reaction is then carried out using the two primers. See *PCR Protocols: A Guide to Methods and Applications*. (Innis, M, Gelfand, D., Sninsky, J. and White, T., eds.), Academic Press, San Diego (1990). Primers can be selected to amplify the entire regions encoding a full-length CAIR protein or to amplify smaller DNA segments as desired.

PCR can be used in a variety of protocols to isolate cDNA's encoding the CAIR proteins. Generally appropriate primers and probes for amplifying DNA encoding CAIR proteins are generated from analysis of the DNA sequences encoding CAIR proteins, such as that found in Seq. Id. No. 1. For example, the oligonucleotides complementary to regions of Sequence Id No. 1 can be used in a PCR protocol to amplify regions of DNA's encoding CAIR proteins. Once such regions are PCR-amplified, they can be sequenced and oligonucleotide probes can be prepared from sequence obtained. These probes can then be used to isolate DNA's encoding CAIR proteins. CAIR proteins can be isolated from a variety of different tissues using this procedure.

A preferred approach for DNA isolation is 5' RACE. Briefly, this technique involves using PCR to amplify a DNA sequence using a random 5' primer and a defined 3' primer. The amplified sequence is then subcloned into a vector where it is then sequenced using standard techniques. The 5' RACE method is well known to those of skill in the art and kits to perform 5' RACE are commercially available (e.g. 5' RACE System, GibcoBRL, Grand Island, N.Y., U.S.A.).

There are numerous other methods of isolating the DNA sequences encoding the CAIR resistance proteins. For example, DNA may be isolated from a genomic or cDNA library using labelled oligonucleotide probes having sequences complementary to the sequences disclosed herein (Seq. Id No. 1). For example, full-length probes may be used, or oligonucleotide probes consisting of subsequences of Seq. Id No. 1 may be used. Such probes can be used directly in hybridization assays to isolate DNA encoding CAIR proteins. Alternatively probes can be designed for use in amplification techniques such as PCR, and DNA encoding CAIR proteins may be isolated by using methods such as PCR (see below).

To prepare a cDNA library, mRNA is isolated from tissue such as heart, skeletal muscle, or cell lines that show CAI resistance. cDNA is prepared from the mRNA and ligated into a recombinant vector. The vector is transfected into a recombinant host for propagation, screening and cloning. Methods for making and screening cDNA libraries are well known. See Gubler and Hoffman, *Gene* 25:263–269, (1983) and Sambrook, et al.

For a genomic library, the DNA is extracted from the tissue or cell line and either mechanically sheared or enzymatically digested to yield fragments of about 12–20 kb. The fragments are then separated by gradient centrifugation from undesired sizes and are constructed in bacteriophage lambda vectors or other vectors. These vectors and phage are packaged in vitro, as described in Sambrook, et al. Recombinant phage are analyzed by plaque hybridization as described in Benton and Davis, *Science*, 196: 180–182 (1977). Colony hybridization is carried out as generally described in M. Grunstein et al. *Proc. Natl. Acad. Sci. U.S.A..*, 72:3961–3965 (1975).

DNA encoding an CAIR protein is identified in either cDNA or genomic libraries by its ability to hybridize with nucleic acid probes, for example on Southern blots, and these DNA regions are isolated by standard methods familiar to those of skill in the art. Alternatively, RNA encoding CAIR proteins may be identified by its ability to hybridize with nucleic acid probes in Northern blots. See Sambrook, et al.

Oligonucleotides for use as probes are chemically synthesized according to the solid phase phosphoramidite triester method first described by Beaucage and Carruthers, *Tetra. Lett.*, 22:1859–1862 (1981) using an automated synthesizer, as described in Needham-VanDevanter, et al., *Nucleic Acids Res.*, 12:6159–6168 (1984). Purification of oligonucleotides is by either native acrylamide gel electrophoresis or by anion-exchange HPLC as described in Pearson and Regnier, *J. Chrom.*, 255:137–149 (1983). The sequence of the synthetic oligonucleotide can be verified using the chemical degradation method of Maxam and Gilbert, in Grossman, L. and Moldave, D., eds. Academic Press, New York, *Methods in Enzymology*, 65:499–560 (1980).

Other methods known to those of skill in the art may also be used to isolate DNA encoding the CAIR protein. See Sambrook, et al. for a description of other techniques for the isolation of DNA encoding specific protein molecules.

D. Expression of CAIR Proteins

Once DNA encoding CAIR proteins is isolated and cloned, one can express the CAIR proteins in a variety of recombinantly engineered cells. It is expected that those of skill in the art are knowledgeable in the numerous expression systems available for expression of DNA encoding CAIR proteins.

In brief summary, the expression of natural or synthetic nucleic acids encoding CAIR proteins will typically be achieved by operably linking the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of polynucleotide sequence encoding CAIR proteins. To obtain high level expression of a cloned gene, such as those polynucleotide sequences encoding CAIR proteins, it is desirable to construct expression plasmids which contain, at the minimum, a strong promoter to direct transcription, a ribosome binding site for translational initiation, and a transcription/translation terminator. The expression vectors may also comprise generic expression cassettes containing at least one independent terminator sequence, sequences permitting replication of the plasmid in both eukaryotes and prokaryotes, i.e., shuffle vectors, and selection markers for both prokaryotic and eukaryotic systems. See Sambrook et al. Examples of expression of CAIR proteins in both prokaryotic and eukaryotic systems are described below.

1. Expression in Prokaryotes

A variety of procaryotic expression systems may be used to express CAIR proteins. Examples include *E. coli*, Bacillus, Streptomyces, and the like. For example, CAIR proteins may be expressed in *E. coli*.

It is essential to construct expression plasmids which contain, at the minimum, a strong promoter to direct transcription, a ribosome binding site for translational initiation, and a transcription/translation terminator. Examples of regulatory regions suitable for this purpose in *E. coli* are the promoter and operator region of the *E. coli* tryptophan biosynthetic pathway as described by Yanofsky, *J. Bacteriol.*, 158: 1018–1024 (1984) and the leftward promoter of phage lambda (Pλ) as described by Herskowitz, et al., *Ann. Rev. Genet.*, 14:399–445 (1980). The inclusion of selection markers in DNA vectors transformed in *E. coli* is also useful. Examples of such markers include genes specifying resistance to ampicillin, tetracycline, or chloramphenicol. See Sambrook et al. for details concerning selection markers for use in *E. coli*.

CAIR proteins produced by prokaryotic cells may not necessarily fold properly. During purification from *E. coli*, the expressed protein may first be denatured and then renatured. This can be accomplished by solubilizing the bacterially produced proteins in a chaotropic agent such as guanidine HCl and reducing all the cysteine residues with a reducing agent such as beta-mercaptoethanol. The protein is then renatured, either by slow dialysis or by gel filtration. See U.S. Pat. No. 4,511,503.

Detection of the expressed antigen is achieved by methods known in the art as radioimmunoassay, or Western blotting techniques or immunoprecipitation. Purification from *E. coli* can be achieved following procedures described in U.S. Pat. No. 4,511,503.

2. Expression in Eukaryotes

A variety of eukaryotic expression systems such as yeast, insect cell lines, bird, fish, and mammalian cells, are known to those of skill in the art. As explained briefly below, CAIR proteins may be expressed in these eukaryotic systems.

Synthesis of heterologous proteins in yeast is well known. *Methods in Yeast Genetics*, Sherman, et al., Cold Spring Harbor Laboratory, (1982) is a well recognized work describing the various methods available to produce the protein in yeast.

Suitable vectors usually have expression control sequences, such as promoters, including 3-phosphoglycerate kinase or other glycolytic enzymes, and an origin of replication, termination sequences and the like as desired. For instance, suitable vectors are described in the literature (Botstein, et al., 1979, *Gene,* 8:17–24; Broach, et al., 1979, *Gene,* 8:121–133).

Two procedures are used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in the papers by J. D. Beggs, 1978, *Nature* (London), 275: 104–109; and Hinnen, et al., *Proc. Natl. Acad. Sci. U.S.A.,* 75:1929–1933 (1978). The second procedure does not involve removal of the cell wall. Instead the cells are treated with lithium chloride or acetate and PEG and put on selective plates (Ito, et al., *J. Bact.,* 153: 163–168 (1983)).

CAIR proteins, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The sequences encoding CAIR proteins can also be ligated to various expression vectors for use in transforming cell cultures of, for instance, mammalian, insect, bird or fish origin. Illustrative of cell cultures useful for the production of the polypeptides are mammalian cells. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines, and various human cells such as COS cell lines, HeLa cells, myeloma cell lines, Jurkat cells, etc. Expression vectors for these cells can include expression control sequences, such as an origin of replication, a promoter (e.g., the CMV promoter, a HSV tk promoter or pgk (phosphoglycerate kinase) promoter), an enhancer (Queen et al., *Immunol. Rev.* 89:49 (1986)), and necessary processing information sites, such as ribosome binding sites, RNA splice sites, polyadenylation sites (e.g., an SV40 large T Ag poly A addition site), and transcriptional terminator sequences. Other animal cells useful for production of CAIR proteins are available, for instance, from the American Type Culture Collection Catalogue of Cell Lines and Hybridomas (7th edition, 1992).

Appropriate vectors for expressing CAIR proteins in insect cells are usually derived from the SF9 baculovirus. Suitable insect cell lines include mosquito larvae, silkworm, armyworm, moth and Drosophila cell lines such as a Schneider cell line (See Schneider *J. Embryol. Exp. Morphol.* 27:353–365 (1987).

As indicated above, the vector, e.g., a plasmid, which is used to transform the host cell, preferably contains DNA sequences to initiate transcription and sequences to control the translation of the protein. These sequences are referred to as expression control sequences.

As with yeast, when higher animal host cells are employed, polyadenylation or transcription terminator sequences from known mammalian genes need to be incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, et al., *J. Virol.* 45:773–781 (1983)).

Additionally, gene sequences to control replication in the host cell may be incorporated into the vector such as those found in bovine papilloma virus type-vectors. Saveria-Campo, *Bovine Papilloma Virus DNA a Eukaryotic Cloning Vector",* pages 213–238 in *DNA Cloning Vol. II a Practical Approach* Ed. D. M. Glover, IRL Press, Arlington, Va. (1985).

The host cells are competent or rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation and microinjection of the DNA directly into the cells.

The transformed cells are cultured by means well known in the art. *Biochemical Methods in Cell Culture and Virology,* Kuchler, R. J., Hutchinson and Ross, Inc., (1977). The expressed polypeptides are isolated from cells grown as suspensions or as monolayers. The latter are recovered by well known mechanical, chemical or enzymatic means.

E. Purification of CAIR Proteins

The polypeptides produced by recombinant DNA technology may be purified by standard techniques well known to those of skill in the art. Recombinantly produced polypeptides can be directly expressed or expressed as a fusion protein. The protein is then purified by a combination of cell lysis (e.g., sonication) and affinity chromatography. For fusion products, subsequent digestion of the fusion protein with an appropriate proteolytic enzyme releases the desired polypeptide.

The polypeptides of this invention may be purified to substantial purity by standard techniques well known in the art, including selective precipitation with such substances as ammonium sulfate, column chromatography, immunopurification methods, and others. See, for instance, R. Scopes, *Protein Purification: Principles and Practice,* Springer-Verlag: New York (1982), incorporated herein by reference. For example, antibodies may be raised to the CAIR proteins as described herein. Cell membranes are isolated from a cell line expressing the recombinant protein, the protein is extracted from the membranes and immunoprecipitated. The proteins may then be further purified by standard protein chemistry techniques as described above.

F. Detection of Nucleotides Encoding CAIR Proteins

The present invention provides methods for detecting DNA or RNA encoding CAIR proteins and for measuring the proteins by immunoassay techniques. These methods are useful for two general purposes. First, assays for detection of nucleic acids encoding CAIR proteins are Useful for the isolation of these nucleic acids from a variety of vertebrate species according to the methods described in section (C) above and by use of the nucleic acid hybridization assays described below. Second, assays for the detection of nucleic acids encoding CAIR proteins provide a means for detecting CAI resistance in a biological sample.

A variety of methods for specific DNA and RNA measurement using nucleic acid hybridization techniques are known to those of skill in the art. See Sambrook, et al. For example, one method for evaluating the presence or absence of DNA encoding CAIR proteins in a sample involves a Southern transfer.

Briefly, the digested genomic DNA is run on agarose slab gels in buffer and transferred to membranes. Hybridization is carried out using the nucleic acid probes discussed above. As described above, nucleic acid probes are designed based on the nucleic acid sequences encoding CAIR proteins (See Seq. I.D. No. 1). The probes can be full length or less than the full length of the nucleic acid sequence encoding the CAIR protein. Shorter probes are empirically tested for specificity. Preferably nucleic acid probes are 20 bases or longer in length. (See Sambrook, et al. for methods of selecting nucleic acid probe sequences for use in nucleic acid hybridization.) Visualization of the hybridized portions allows the qualitative determination of the presence or absence of DNA encoding CAIR proteins.

Similarly, a Northern transfer may be used for the detection of mRNA encoding CAIR proteins. In brief, the mRNA is isolated from a given cell sample using, for example, an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify the presence or absence of CAIR proteins.

A variety of nucleic acid hybridization formats are known to those skilled in the art. For example, common formats include sandwich assays and competition or displacement assays. Hybridization techniques are generally described in "Nucleic Acid Hybridization, A Practical Approach," Ed. Hames, B. D. and Higgins, S. J., IRL Press, (1985); Gall and Pardue Proc. Natl. Acad. Sci., U.S.A., 63:378–383 (1969); and John et al., Nature, 223:582–587 (1969).

For example, sandwich assays are commercially useful hybridization assays for detecting or isolating nucleic acid sequences. Such assays utilize a "capture" nucleic acid covalently immobilized to a solid support and a labelled "signal" nucleic acid in solution. The clinical sample will provide the target nucleic acid. The "capture" nucleic acid and "signal" nucleic acid probe hybridize with the target nucleic acid to form a "sandwich" hybridization complex. To be effective, the signal nucleic acid cannot hybridize with the capture nucleic acid.

Typically, labelled signal nucleic acids are used to detect hybridization. Complementary nucleic acids or signal nucleic acids may be labelled by any one of several methods typically used to detect the presence of hybridized polynucleotides. The most common method of detection is the use of autoradiography with $^3H$, $^{125}I$, $^{35}S$, $^{14}C$, or $^{32}P$-labelled probes or the like. Other labels include ligands which bind to labelled antibodies, fluorophores, chemiluminescent agents, enzymes, and antibodies which can serve as specific binding pair members for a labelled ligand.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal.

The label may also allow indirect detection of the hybridization complex. For example, where the label is a hapten or antigen, the sample can be detected by using antibodies. In these systems, a signal is generated by attaching fluorescent or enzyme molecules to the antibodies or, in some cases, by attachment to a radioactive label. (Tijssen, P., "Practice and Theory of Enzyme Immunoassays," Laboratory Techniques in Biochemistry and Molecular Biology, Burdon, R. H., van Knippenberg, P. H., Eds., Elsevier (1985), pp. 9–20.)

The sensitivity of the hybridization assays may be enhanced through use of a nucleic acid amplification system which multiplies the target nucleic acid being detected. Examples of such systems include the polymerase chain reaction (PCR) system and the ligase chain reaction (LCR) system. Other methods recently described in the art are the nucleic acid sequence based amplification (NASBA™, Cangene, Mississauga, Ontario) and Q Beta Replicase systems.

An alternative means for determining the level of expression of a gene encoding an CAIR protein is in situ hybridization. In situ hybridization assays are well known and are generally described in Angerer, et al., Methods Enzymol., 152:649–660 (1987). In an in situ hybridization assay, cells or tissue specimens are fixed to a solid support, typically a glass slide. If DNA is to be probed, the cells are denatured with heat or alkali. The cells are then contacted with a hybridization solution at a moderate temperature to permit annealing of labeled probes specific to CAIR proteins. The probes are preferably labelled with radioisotopes or fluorescent reporters.

G. Detection of CAIR Proteins by Immunoassay

In addition to detecting expression of nucleic acids encoding CAIR proteins by nucleic acid hybridization, one can also use immunoassays to detect the proteins. Immunoassays can be used to qualitatively or quantitatively analyze for the proteins. A general overview of the applicable technology can be found in Harlow and Lane, Antibodies: A Laboratory Manual, Cold Spring Harbor Pubs., N.Y. (1988), incorporated herein by reference.

1. Antibody Production

A number of immunogens may be used to produce antibodies specifically reactive with CAIR proteins. Recombinant protein is the preferred immunogen for the production of monoclonal or polyclonal antibodies. Naturally occurring protein may also be used either in pure or impure form. Synthetic peptides made using CAIR-1 sequences described herein may also used as an immunogen for the production of antibodies to the protein. Recombinant protein can be expressed in eukaryotic or prokaryotic cells as described above, and purified as generally described above. The product is then injected into an animal capable of producing antibodies. Either monoclonal or polyclonal antibodies may be generated, for subsequent use in immunoassays to measure the protein.

Methods of production of polyclonal antibodies are known to those of skill in the art. In brief, an immunogen, preferably a purified protein, is mixed with an adjuvant and animals are immunized. The animal's immune response to the immunogen preparation is monitored by taking test bleeds and determining the liter of reactivity to the CAIR protein. When appropriately high liters of antibody to the immunogen are obtained, blood is collected from the animal and antisera are prepared. Further fractionation of the antisera to enrich for antibodies reactive to the protein can be done if desired. (See Harlow and Lane, supra).

Monoclonal antibodies may be obtained by various techniques familiar to those skilled in the art. Briefly, spleen cells from an animal immunized with a desired antigen are immortalized, commonly by fusion with a myeloma cell (See, Kohler and Milstein, Eur. J. Immunol. 6:511–519 (1976), incorporated herein by reference). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al. Science 246:1275–1281 (1989).

Methods of production of synthetic peptides are known to those of skill in the art. Briefly, the predicted immunogenic regions of the CAIR protein sequences described herein are identified. Peptides preferably at least 10 amino acids in length are synthesized corresponding to these regions and the peptides are conjugated to larger protein molecules for subsequent immunization. Preferably, peptide sequences corresponding to unique regions of an CAIR proteins are used to generate antibodies specifically immunoreactive with the CAIR proteins. Production of monoclonal or polyclonal antibodies is then carried out as described above.

2. Immunoassays

A particular protein can be measured by a variety of immunoassay methods. For a review of immunological and immunoassay procedures in general, see *Basic and Clinical Immunology* 7th Edition, D. Stites and A. Terr ed. (1991). Moreover, the immunoassays of the present invention can be performed in any of several configurations, which are reviewed extensively in *Enzyme Immunoassay*, E. T. Maggio, ed., CRC Press, Boca Raton, Fla. (1980); "Practice and Theory of Enzyme Immunoassays," P. Tijssen, *Laboratory Techniques in Biochemistry and Molecular Biology*, Elsevier Science Publishers B.V. Amsterdam (1985); and, Harlow and Lane, *Antibodies, A Laboratory Manual*, supra, each of which is incorporated herein by reference.

Immunoassays for measurement of CAIR proteins can be performed by a variety of methods known to those skilled in the art. In brief, immunoassays to measure the protein can be either competitive or noncompetitive binding assays. In competitive binding assays, the sample analyte competes with a labeled analyte for specific binding sites on a capture agent bound to a solid surface. Preferably the capture agent is an antibody specifically reactive with CAIR proteins produced as described above. The concentration of labeled analyte bound to the capture agent is inversely proportional to the amount of free analyte present in the sample.

In a competitive binding immunoassay, the CAIR protein present in the sample competes with labelled protein for binding to a specific binding agent, for example, an antibody specifically reactive with the CAIR protein. The binding agent may be bound to a solid surface to effect separation of bound labelled protein from the unbound labelled protein. Alternately, the competitive binding assay may be conducted in liquid phase and any of a variety of techniques known in the art may be used to separate the bound labelled protein from the unbound labelled protein. Following separation, the amount of bound labeled protein is determined. The amount of protein present in the sample is inversely proportional to the amount of labelled protein binding.

Alternatively, a homogenous immunoassay may be performed in which a separation step is not needed. In these immunoassays, the label on the protein is altered by the binding of the protein to its specific binding agent. This alteration in the labelled protein results in a decrease or increase in the signal emitted by label, so that measurement of the label at the end of the immunoassay allows for detection or quantitation of the protein.

CAIR proteins may also be detected and quantified by a variety of noncompetitive immunoassay methods. For example, a two-site, solid phase sandwich immunoassay is used. In this type of assay, a binding agent for the protein, for example an antibody, is attached to a solid phase. A second protein binding agent, which may also be an antibody, and which binds the protein at a different site, is labelled. After binding at both sites on the protein has occurred, the unbound labelled binding agent is removed and the amount of labelled binding agent bound to the solid phase is measured. The amount of labelled binding agent bound is directly proportional to the amount of protein in the sample. Alternatively, CAIR proteins may be detected using immunoprecipitation methods as described by Otto et al. pages 119 to 127 in *Methods in Cell Biology Volume 37: Antibodies in Cell Biology*, Asai, ed., Academic Press, New York (1993).

Western blot analysis can also be done to determine the presence of CAIR proteins in a sample. Electrophoresis is carded out, for example, on a tissue sample suspected of containing the protein. Following electrophoresis to separate the proteins, and transfer of the proteins to a suitable solid support such as a nitrocellulose filter, the solid support is then incubated with an antibody reactive with the protein. This antibody may be labelled, or alternatively may be it may be detected by subsequent incubation with a second labelled antibody that binds the primary antibody.

The immunoassay formats described above employ labelled assay components. The label can be in a variety of forms. The label may be coupled directly or indirectly to the desired component of the assay according to methods well known in the art. A wide variety of labels may be used. The component may be labelled by any one of several methods. Traditionally a radioactive label incorporating $^3H$, $^{125}I$, $^{35}S$, $^{14}C$, or $^{32}P$ was used. Non-radioactive labels include ligands which bind to labelled antibodies, fluorophores, chemiluminescent agents, enzymes, and antibodies which can serve as specific binding pair members for a labelled ligand. The choice of label depends on sensitivity required, ease of conjugation with the compound, stability requirements, and available instrumentation. For a review of various labeling or signal producing systems which may be used, see U.S. Pat. No. 4,391,904, which is incorporated herein by reference.

Antibodies reactive with a particular protein can also be measured by a variety of immunoassay methods. For a review of immunological and immunoassay procedures applicable to the measurement of antibodies by immunoassay techniques, see *Basic and Clinical Immunology* 7th Edition (D. Stites and A. Terr ed.) supra, *Enzyme Immunoassay*, E. T. Maggio, ed., supra, and Harlow and Lane, *Antibodies, A Laboratory Manual*, supra.

In brief, immunoassays to measure antisera reactive with CAIR proteins can be either competitive or noncompetitive binding assays. In competitive binding assays, the sample analyte competes with a labeled analyte for specific binding sites on a capture agent bound to a solid surface. Preferably the capture agent is a purified recombinant CAIR protein produced as described above. Other sources of CAIR proteins, including isolated or partially purified naturally occurring protein, may also be used. Noncompetitive assays are typically sandwich assays, in which the sample analyte is bound between two analyte-specific binding reagents. One of the binding agents is used as a capture agent and is bound to a solid surface. The second binding agent is labelled and is used to measure or detect the resultant complex by visual or instrument means. A number of combinations of capture agent and labelled binding agent can be used. A variety of different immunoassay formats, separation techniques and labels can be also be used similar to those described above for the measurement of CAIR proteins.

This invention also embraces kits for detecting the presence of CAIR proteins in tissue or blood samples which comprise a container containing antibodies selectively immunoreactive to the protein and instructional material for performing the test. The kit may also contain other components such as CAIR proteins, controls, buffer solutions, and secondary antibodies.

This invention further embraces kits for detecting DNA or RNA encoding CAIR proteins in tissue or blood samples which comprise nucleic probes as described herein and instructional material. The kit may also contain additional components such as labeled compounds, as described herein, for identification of duplexed nucleic acids.

H. Detecting CAIR Resistance

A common problem in the treatment of various cancers is the acquisition of resistance by the tumor cells to the particular pharmaceutical to which they are exposed. It is desirable during therapy to assay for the acquisition of resistance to a particular pharmaceutical in order to gauge the efficacy of treatment or to determine when to halt or alter particular treatment protocols.

As shown in Example 1, tumor cells are capable of developing resistance to CAI. The development of this resistance involves up-regulation of CAIR gene and consequent expression of CAIR proteins. Thus, both increased levels of CAIR mRNA and CAIR proteins provide convenient markers to detect the onset of CAI resistance.

This invention provides for assays to detect CAI resistance. These assays require detecting the increased expression of CAIR proteins in the sample tissues relative to the same tissues prior to their exposure to CAI and its functional equivalents. In a preferred embodiment, these assays require obtaining a biological sample (e.g. tumor biopsy or blood sample) prior to commencing a therapeutic regimen. During treatment with CAI or functional equivalents, subsequent samples will be taken and assayed for CAIR production. Where CAIR production shows an increase relative to the initial (pre-CAI) samples, one may infer the onset of CAI resistance.

CAIR production may be assayed by detecting expression levels of CAIR mRNA or CAIR proteins. Means for detecting CAIR mRNA are described in section (F), while means for detection CAIR proteins are described in section (G). In a preferred embodiment, mRNA will be detected using hybridization probes, while CAIR proteins will be detected using immunoassays.

I. Use of CAI Resistant Cells in Screening for Resistance Modulators

The CAI resistant cells of the present invention may be utilized as in a bioassay to screen for compounds that reduce or fully obviate CAI resistance. Generally such an assay will comprise culturing CAI resistant cells in the presence of fixed or varying concentrations of the compounds to be screened and CAI or functionally equivalent molecules. Where the screened compounds reduce CAI resistance, the growth rate of the cells will decrease or the cells may die. Means of determining cell growth rate are well known to those of skill in the art and include, for example, measuring changes in the uptake of labeled metabolic substrates (e.g. [$^3$H]-thymidine) or by cell counts.

This invention further embraces kits for screening compositions or combinations of compositions for therapeutic efficacy in CAI resistant cells which comprise CAI resistant cells as described herein and instructional material. The kit may also contain additional components such culture media, labeled sustrates for assessing metabolic activity of the resistant cells as described herein.

J. Pharmacological Compositions

The nucleic acid sequences encoding the CAIR proteins and the CAIR proteins themselves may be utilized to produce anti-sense, antibody, and single chain peptide pharmacological compositions. The nucleotide sequence encoding CAI may be used to produce anti-sense therapeutics. These are molecules that bind to mRNA transcribed from the CAIR gene and form heteroduplex molecules that prevent further translation and thereby inhibit the expression of CAIR proteins causing the cell to loose its CAI resistance. Methods of producing anti-sense molecules are well known to those of skill in the art. See, for example, Cohen, et al., U.S. Pat. Nos. 5,264,423 and 5,276,019; Miller, et al., U.S. Pat. Nos. 4,469,863, and 4,757,055; and Uhlmann, et al. *Chem. Rev.*, 90:543–584 (1990).

Alternatively, the CAIR protein or fragments thereof may be used as an immunogen to generate antibodies specific to the CAIR protein as described above. The antibodies will bind to the CAIR protein thereby preventing the normal interaction of that protein with other cellular constituents. Again, the cell will loose its CAI resistance. Methods of using antibodies to block normal protein function are also well known to those of skill in the art. See, for example, El-Badry, et al., *Cell Growth and Diff.*, 1: 325–331 (1990).

The CAIR proteins may be used to make non-functional mimics that compete with the normal CAIR proteins and thereby reduce or modulate the effect of CAIR proteins. Means of producing disfunctional mimetics include the substitution or chemical modification of critical amino acid residues. Substitution of amino acids may be accomplished directly during the chemical synthesis or CAIR proteins, or if the proteins are recombinantly expressed by using methods of site directed mutagenesis to alter the nucleotide sequence encoding particular residues. Means of production of peptide mimetics are well known to those of skill in the art. For example the drug BB94 is a peptide mimetic that inhibits the enzyme collagenase and is used as a metastisis inhibitor.

As described above in section (B), the CAIR-1 resistance protein contains a number of SH3 domain binding sites. SH3 domains have been implicated in a number of cellular signaling pathways as well as cytoskeletal activity. The CAIR protein or fragments thereof carrying the SH3 binding domains may be used to selectively bind and block SH3 domains thereby inhibiting specific signal transduction pathways. This is useful in the treatment of certain diseases characterized by abnormal signaling such as cancer, hyperproliferative states, correction of collagen vascularities (e.g. lupis and rheumatoid arthritis), nephropathies, neruopathies (e.g. ALF, Alzheimers disease), and myopathies (e.g. cardiomyopathies, skeletalmyopathies).

The pharmaceutical compositions of this invention are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration which comprise a solution of the agents described above dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyopholized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient and more preferably at a concentration of 25%–75%.

For aerosol administration, the polypeptides, antibodies, or antisense molecules are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

In therapeutic applications, antisense molecules, antibodies, or polypeptides of the invention are administered to a patient in an amount sufficient to block expression of CAIR proteins or to block particular signal transduction pathways. An amount adequate to accomplish this is defined as "therapeutically effective dose." Amounts effective for this use will depend on, e.g., the particular antisense molecule, antibody, or polypeptide, the manner of administration, the weight and general state of health of the patient, and the judgment of the prescribing physician.

K. Gene Therapy Applications

A variety of human diseases may be treated by therapeutic approaches that involve stably introducing a gene into a human cell such that the gene may be transcribed and the gene product may be produced in the cell. Diseases amenable to treatment by this approach include inherited diseases, particularly those diseases such as GSD Type 1a where the defect is with a single gene. For discussions on the application of gene therapy towards the treatment of genetic as well as acquired diseases See Miller, A. D. (1992) *Nature* 357:455–460, and Mulligan, R. C. (1993) *Science* 260:926–932, both incorporated herein by reference.

This invention contemplates the use of gene therapy to introduce CAIR genes into healthy cells so that they are spared and permit the exposure of unhealthy, e.g. tumor cells, to higher doses of CAI while reducing systemic toxicity. Alternatively, gene therapy may be used to introduce genes encoding CAI mimetics that compete with CAI and thereby reduce the level of CAI resistance of diseased cells rendering them more susceptible to CAI therapy.

Delivery of the gene or genetic material into the cell is the first critical step in gene therapy treatment of disease. A variety of methods have been used experimentally. Most research has focused on the use of retroviral and adenoviral vectors for gene delivery into the cell. Retroviral vectors have the ability to stably integrate the transferred gene sequences into the chromosomal DNA of the target cell. Retroviral vectors are particularly attractive because they are very efficient in stably transducing a high percentage of target cells. Accordingly most of the approved gene therapy clinical protocols use retroviral vectors. See Miller, A. D., (1992) supra. Retroviral vectors are particularly useful for modifying cells because of the high efficiency with which the retroviral vectors transduce target cells and integrate into the target cell genome. Additionally, the retroviruses harboring the retroviral vector are capable of infecting cells from a wide variety of tissues.

Retroviral vectors are produced by genetically manipulating retroviruses. Retroviruses are called RNA viruses because the viral genome is RNA. Upon infection, this genomic RNA is reverse transcribed into a DNA copy which is integrated into the chromosomal DNA of transduced cells with a high degree of stability and efficiency. The integrated DNA copy is referred to as a provirus and is inherited by daughter cells as is any other gene. The wild type retroviral genome and the proviral DNA have three genes: the gag, the pol and the env genes, which are flanked by two long terminal repeat (LTR) sequences. The gag gene encodes the internal structural (nucleocapsid) proteins; the pol gene encodes the RNA directed DNA polymerase (reverse transcriptase); and the env gene encodes viral envelope glycoproteins. The 5' and 3' LTRs serve to promote transcription and polyadenylation of virion RNAs. Adjacent to the 5' LTR are sequences necessary for reverse transcription of the genome (the tRNA primer binding site) and for efficient encapsulation of viral RNA into particles (the Psi site). See Mulligan, R. C., In: *Experimental Manipulation of Gene Expression*, M. Inouye (ed), 155–173 (1983); Mann, R., et al., *Cell*, 33:153–159 (1983); Cone, R. D. and R. C. Mulligan, *Proc. Natl. Acad. Sci., U.S.A.*, 81:6349–6353 (1984).

The design of retroviral vectors is well known to one of skill in the art. See Singer, M. and Berg, P. supra. In brief, if the sequences necessary for encapsidation (or packaging of retroviral RNA into infectious virions) are missing from the viral genome, the result is a cis acting defect which prevents encapsidation of genomic RNA. However, the resulting mutant is still capable of directing the synthesis of all virion proteins. Retroviral genomes from which these sequences have been deleted, as well as cell lines containing the mutant genome stably integrated into the chromosome are well known in the art and are used to construct retroviral vectors. Preparation of retroviral vectors and their uses are described in many publications including European Patent Application EPA 0 178 220, U.S. Pat. No. 4,405,712, Gilboa, *Biotechniques* 4:504–512 (1986), Mann, et al., *Cell* 33:153–159 (1983), Cone and Mulligan, *Proc. Natl. Acad. Sci. U.S.A.* 81:6349–6353 (1984), Eglitis, M. A, et al. (1988) *Biotechniques* 6:608–614, Miller, A. D. et al. (1989) *Biotechniques* 7:981–990, Miller, A. D.(1992) *Nature*, supra, Mulligan, R. C. (1993), supra. and Gould, B. et al., and International Patent Application No. WO 92/07943 entitled "Retroviral Vectors Useful in Gene Therapy". The teachings of these patents and publications are incorporated herein by reference.

The retroviral vector particles are prepared by recombinantly inserting the gene encoding CAIR proteins or non-functional CAIR protein mimetics into a retrovirus vector and packaging the vector with retroviral capsid proteins by use of a packaging cell line. The resultant retroviral vector particle is incapable of replication in the host cell and is capable of integrating into the host cell genome as a proviral sequence containing the CAIR gene or CAIR non-functional mimetic. As a result, the patient is capable of producing normal CAIR and resisting the effects of calcium influx inhibitors or alternatively, the production of non-functional CAIR mimetics prevents the onset of CAI resistance.

Packaging cell lines are used to prepare the retroviral vector particles. A packaging cell line is a genetically constructed mammalian tissue culture cell line that produces the necessary vital structural proteins required for packaging, but which is incapable of producing infectious virions. Retroviral vectors, on the other hand, lack the structural genes but have the nucleic acid sequences necessary for packaging. To prepare a packaging cell line, an infectious clone of a desired retrovirus, in which the packaging site has been deleted, is constructed. Cells comprising this construct will express all structural proteins but the introduced DNA will be incapable of being packaged. Alternatively, packaging cell lines can be produced by transforming a cell line with one or more expression plasmids encoding the appropriate core and envelope proteins. In these cells, the gag, pol, and env genes can be derived from the same or different retroviruses.

A number of packaging cell lines suitable for the present invention are also available in the prior art. Examples of these cell lines include Crip, GPE86, PA317 and PG13. See Miller et al., *J. Virol.* 65:2220–2224 (1991), which is incorporated herein by reference. Examples of other packaging cell lines are described in Cone and Mulligan, *Proc. Natl. Acad. Sci. U.S.A.*, 81:6349–6353 (1984) and in Danos and Mulligan, *Proc. Natl. Acad. Sci. U.S.A.*, 85:6460–6464 (1988), Eglitis, et al. (1988) supra and Miller, (1990) supra, also all incorporated herein by reference.

Packaging cell lines capable of producing retroviral vector particles with chimeric envelope proteins may be used. Alternatively, amphotropic or xenotropic envelope proteins, such as those produced by PA317 and GPX packaging cell lines may be used to package the retroviral vectors.

The following examples are offered by way of illustration, not by way of limitation.

EXAMPLES

Example 1

Culture of CAI Resistant Cells

Carboxyamido-triazole (CAI) has been observed to inhibit malignant proliferation, invasion, and metastasis of cancer cells, suggesting the role of CAI, and related compounds, as potential cancer therapeutics. Of concern in the development and utilization of cancer therapeutics is the development of resistance by tumor cells to the particular pharmacological regimen to which they are exposed. Thus, it was desired to develop, cells that express a resistance to CAI both as a model system for examining mechanisms of CAI resistance and to provide an assay or screening system for treatment regimens that reduce or eliminate resistance to CAI and its analogues.

Low passage (passage 13) parental human melanoma cells (A2058), and human ovarian cancer cells (OVCAR3) were cultured in Dulbecco's Modified Eagles medium (DMEM) supplemented with 10% fetal calf serum (FCS) and pen/strep (penicillin and streptomycin). Over a period of 24 to 30 months, the cells were incubated with increasing concentrations of CAI starting with 0.1 µM and reaching 45 µM. The CAI, obtained from the Developmental Therapeutics Program of the National Cancer Institute, was dissolved in DMSO and aliquots were stored at −70° C. until used. The diluted CAI was added directly into the media as required. Continuous selective pressure with CAI was maintained throughout culture and was maintained throughout all experiments.

It was found that A2058 cells chronically resistant to 10 µM (10R), 20 µM (20R), 30 µM (30R), and 40 µM (40R) were obtained. No overt differences in morphology of the A2058 CAI resistant cells was observed. The growth rate of A2058 CAI resistant cells was not attenuated until the 40 µM treatment in which it decreased somewhat.

OVCAR3 cells chronically resistant to 10 µM and 20 µM CAI were also established. The OVCAR3 cells had slightly lower growth rates in the CAI treatments.

Example 2

Isolation of the CAIR-1 Gene

DNA encoding a protein that correlated with CAI resistance in A2058 cells was isolated by subtraction hybridization according to the method described by Hampson, et al. *Nucleic Acids Res.*, 20:2899 (1992).

RNA was isolated from 20 µM resistant A2058 cells (A2058-20R) and used as a template to synthesize cDNA using reverse transcriptase. The resulting cDNA was purified from the residual RNA by alkaline hydrolysis (0.5M NaOH, 15 minutes, 55° C.) followed by a Sephadex G50 spin column. The cDNA was quantitated using $^{32}$P-dCTP tracer and 500 ng was used for hybridization in solution to 10 µg mRNA obtained from the parental (wild type) cell line (A2058). Hybridization was performed for 20 hours at 68° C. in 10 µL final volume with final concentrations of 0.5M NaCl, 25 mM HEPES buffer, pH 7.5, 5 mM EDTA, and 1% SDS.

After hybridization, the final product was diluted 5-fold with molecular grade double distilled $H_2O$ and then ethanol precipitated (1/10 volume 3 M NaOAc, pH 5.0, 2 vol 100% ethanol, dry ice for 20 minutes or overnight at −20° C.). The resulting pellet was gently washed with 80% ethanol, dried under vacuum, and dissolved in 50 µL buffer (25 mM Tris-HCl, pH 7.0, 1 mM EDTA, 5% DMSO, 2 mM ascorbic acid) and incubated for 3 minutes at 68° C.

To chemically crosslink the mRNA:cDNA heteroduplex, 2,5-diaziridinyl-3,4-benzoquinone (DZQ) was added to a final concentration of 200 µM and the reaction mixture was incubated at 45° C. for 20 minutes. The reaction was then ethanol precipitated as described above, washed and used for probing either Northern blots, genomic DNA, or cDNA libraries. The probe was labelled with $^{32}$P-dCTP using standard random primer techniques as described by Maniatis, et al. *Molecular Cloning: A Laboratory Manual.* Cold Spring Harbor Laboratory Press, NY (1982) which is incorporated herein by reference. The labeling reaction was run at room temperature for 20 minutes using Sequenase II enzyme.

The subtracted probe was first hybridized against a Northern blot of total RNA from parental A2058 cells and CAI resistant A2058-20R cells. Increased expression of a number of transcripts was seen (FIG. 1, upper left panel). Re-hybridization of the blot with radiolabeled GAPDH as a housekeeping gene confirmed the increased expression (FIG. 1, lower left panel).

A cDNA library was constructed from A2058-20R cells by Stratagene (La Jolla, Calif., U.S.A.). The library was probed using standard approaches (Id.) and the positive probes were plaque purified. Forty-one clones were selected and 35 were determined to be nonoverlapping by restriction digest. Fifteen were randomly selected for determination of their expression by Northern analysis. Inserts were purified by low melting point agarose gel electrophoresis and then radiolabeled with standard random primer conditions (Amersham, Little Chalfont, Bucks, United Kingdom) and hybridized with a Northern of parental (wildtype) total RNA and RNA from A2058-20R cells. Of the clones screened, three (Table 1) showed increased expression in response to culture with CAI. Table 1 shows, for each clone, the size of the transcript as determined from the Northern blots (FIG. 1) and the size of the cDNA insert. The CAIR-1 cDNA (clone 21DBB) which showed 3.8 fold (range 2 fold to ~4 fold on replicate Northerns) increased expression compared to the GAPDH housekeeping gene control was selected for sequence analysis. The CAIR-1 cDNA (clone 21DBB insert) was sequenced using standard dideoxy-sequencing (SequenaseII kit) with 35S-dATP label. The cDNA sequence is shown in Seq. Id No. 1.

TABLE 1

Subtraction hybridization results.

| Clone | Transcript Size | cDNA (insert) Size |
|---|---|---|
| 21DBB (CAIR-1) | 2.8 kb | 1.3 kb |
| 13BAA (CAIR-2) | 4.2 kb | 1.9 kb |
| 15CBB (CAIR-3) | 4.5 kb | 2.1 kb |

Example 3

Characterization of CAIR-1

The CAIR-1 cDNA sequence was analyzed using GeneWorks and GeneBank and found to be unique and containing an open reading frame, a polyadenylation signal and a polyA tail indicating that it is the 3' end of a mammalian gene. Translation of the DNA sequence yielded the carboxyl terminus of a protein which is unique by GeneBank and other database comparisons. The CAIR-1 sequence contains a unique proline rich sequence which fulfills the consensus definition for Src homology 3 (SH3) binding proteins. The SH3 domains are common in signaling proteins and have been shown to target to cytoskeleton, membrane and other signaling proteins (Koch, et al., Science 252:668–674 (1991). The SH3 BP domain consensus sequence is: XPXXPPPψXP where positions 2,7, and 10 are obligate P (proline), the X is any amino acid, and the ψ is a hydrophobic amino acid. There are 4 unique versions of the SH3 binding protein consensus sequences in carboxyl terminus of CAIR-1 protein (Table 2).

TABLE 2

SH3 binding protein domain consensus sequences. CAIR-1 A through D were identified in the CAIR protein encoded by clone 21DBB.

| Protein Id | Consensus XPXXPPPψXP | Sequence ID 3 |
|---|---|---|
| CAIR-1 A | KPVSDKPPPP | 4 |
| CAIR-1 B | VPPAPVPCPP | 5 |
| CAIR-1 C | APVPCPPPSP | 6 |
| CAIR-1 D | APAEATPPKP | 7 |
| 3BP-1[1]: | APTMPPPLPP | 8 |

TABLE 2-continued

SH3 binding protein domain consensus sequences. CAIR-1 A through D were identified in the CAIR protein encoded by clone 21DBB.

| Protein Id | Consensus XPXXPPPψXP | Sequence ID 3 |
|---|---|---|
| p85α1[2]: | APPTPKPRPP | 9 |
| p85α2[3]: | QPAPALPPKP | 10 |

[1]Ren, et al. Science 259: 1157–1161 (1993)
[2,3]Kapeller, et al. J. Biol. Chem., 21: 1927–1233 (1994)

Example 4

Expression of CAIR Proteins in Tissues

Commercial Northerns consisting of poly-A RNAs from human heart, brain, placenta, lung, liver, skeletal muscle, kidney, and pancreas, spleen, thymus, prostate, testis, ovary, small intestine, colon, and peripheral blood leukocytes were obtained from Stratagene (La Jolla, Calif., U.S.A.). The preparations were probed with the CAIR-1 probe.

The human tissue distribution of CAIR-1 demonstrated marked expression in heart, skeletal muscle (both known to have important calcium-mediated regulation) and also in placenta, lung, and liver. Less expression was noted in brain, kidney, and pancreas. The expression in prostate, testis, ovary, and colon was minimal.

Example 5

Detection of SH3 Binding Regions in CAIR-1

The cDNA of CAIR-1 containing an SH3 binding domain is subcloned into pGEX-2T vectors at BamHI and EcoRI sites. *Escherichia coil* cells are transformed with the subcloned pGEX2T vector. Expression of the CAIR-1 fusion protein is induced with isopropyl-1-thio-B-D-galactopyranoside. The cells are then lysed and the lysate containing the GST-CAIR-1 fusion proteins are purified using glutathione agarose beads and eluted with Tris-HCl containing reduced glutathione.

The purified GST-CAIR-1 fusion protein is immobilized on glutathione-Sepharose beads. The beads are then incubated at 4° C. (while rocking constantly) with the proteins containing SH3 domains such as Abl, Fyn, Lck and p85. The beads are washed and the eluted proteins are checked using SDS-PAGE, at 4° C. with constant rocking.

The SH3-CAIR-1 complex is then purified by the use of glutathione-Sepharose beads and then electrophoretically separated. SH3 binding complexes can be identified using commercially available SH3 antibodies (antibody to the SH3-containing protein) or by antibody to CAIR-1.

---

What is claimed is:

1. An isolated human nucleic acid encoding a carboxyamido-triazole resistance (CAIR) protein, said nucleic acid capable of hybridizing specifically to the complement of a second nucleic acid consisting of the nucleic acid sequence of SEQ ID NO: 1 in the presence of a human genomic library under stringent conditions, wherein said isolated nucleic acid, when in a cell line, expresses said CAIR protein at higher levels when said cell line is cultured in the presence of at least 10 μM concentration of carboxyamido-triazole (CAI) than when said cell line is cultured under the same culture conditions without CAI, and wherein expression of said nucleic acid is associated with CAI resistance.

2. The nucleic acid of claim 1, said nucleic acid comprising the nucleotide sequence of SEQ ID NO: 1.

3. An isolated nucleic acid encoding a CAIR resistance protein, wherein said protein specifically binds to an antibody generated against an immunogen consisting of the amino acid sequence depicted by Seq. Id No. 2, and wherein said nucleic acid, when in a cell line, expresses said CAIR protein at higher levels when said cell line is cultured in the presence of at least 10 μM concentration of carboxyamido-triazole (CAI) than when said cell line is cultured under the same culture conditions without CAI, and wherein expression of said nucleic acid is associated with CAI resistance.

4. The nucleic acid of claim 3, said nucleic acid comprising the nucleotide sequence of SEQ ID NO: 1.

5. A pharmacological composition that reduces CAI resistance said composition comprising an antisense nucleotide that binds to a nucleic acid of claim 1 encoding a CAIR protein and a pharmaceutically acceptable carrier.

* * * * *